United States Patent [19]

Bodor et al.

[11] Patent Number: 4,892,737

[45] Date of Patent: Jan. 9, 1990

[54] COMPOSITION AND METHOD FOR ENHANCING PERMEABILITY OF TOPICAL DRUGS

[75] Inventors: Nicholas S. Bodor, Gainesville, Fla.; Thorsteinn Loftsson, Reykjavik, Iceland

[73] Assignee: University of Florida, Gainesville, Fla.

[21] Appl. No.: 247,532

[22] Filed: Sep. 22, 1988

[51] Int. Cl.$^4$ ............................ A61K 9/06; A61K 9/22
[52] U.S. Cl. ...................................... 424/449; 514/554; 514/560
[58] Field of Search ........................ 514/554, 558, 560; 424/449

[56] References Cited

U.S. PATENT DOCUMENTS 4,304,765 12/1981 Shell et al. ............................ 424/427
4,460,562 7/1984 Keith et al. ............................ 424/78
4,777,039 10/1988 Lang et al. ............................ 424/70

OTHER PUBLICATIONS

Cooper, "Increased Skin Permeability for Lipophilic Molecules", *Journal of Pharmaceutical Sciences*, vol. 73, No. 8. Aug. 1984, pp. 1153–1156.

Cooper et al., CA:103:59235d "Effect of Fatty Acids and Alcohols on the Penetration of Acyclovir Across Human Skin In Vitro".

Wickett et al., CA:96:187298a, "Penetrating Topical Pharmaceutical Compositions".

*Primary Examiner*—John Kight
*Assistant Examiner*—Nathan M. Nutter
*Attorney, Agent, or Firm*—Dennis P. Clarke

[57] ABSTRACT

A composition and method for enhancing permeability of topical drugs wherein the agent which enhances the permeability of the drug is selected from the group consisting of (1) a choline ester having the formula:

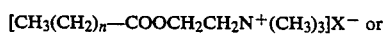

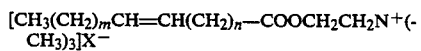

wherein m and n are integers in the range of from 0 to 30 and $X^-$ is a pharmaceutically acceptable anion and (2) a mixture of the choline ester and an acid having the formula:

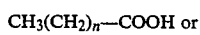

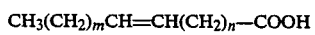

or a pharmaceutically acceptable salt thereof.

24 Claims, No Drawings

COMPOSITION AND METHOD FOR ENHANCING PERMEABILITY OF TOPICAL DRUGS

BACKGROUND OF THE INVENTION

1. Field of the Invention

The present invention relates to the enhancement of the permeability into and through the skin of topically applied drugs.

2. Description of the Prior Art

The bio-activity of a wide variety of drugs render them attractive candidates for topical application to treat a number of conditions. Exemplary of such drugs and their applications are: acyclovir for topical treatment of herpes labilis and gentialis; trifluorothymidine for topical treatment of herpes infections; nitroglycerin (transdermal delivery) for prevention and treatment of anginal attacks; estradiol (and other estrogens) for treatment of various postmenopausal symptoms, such as osteoporosis and vasomotor disturbances; estradiol (and other estrogens) for contraceptive purposes; all-trans-retinoic acid (Tretinoin) for topical treatment of acne; clindamycin for topical treatment of acne; hydrocortisone (and other glucocorticoids) for topical treatment of anti-inflammtory conditions, etc.

Many of the drugs are only poorly absorbed through the skin of both human and non-human animals, however, thereby severely limiting their applicability. A number of agents which enhance the permeability through skin of several drugs have been proposed: Oleic acid—(Cooper, J. Pharm. Sci., Vol. 73, p. 1153 (1984); Loftsson et al, Pharm. Res., Vol. 4, p. 436 (1987));

Azone—(Spruance et al, Antimicrob. Agents Chemother., Vol. 26, p. 819 (1984);,

Dimethyl sulfoxide (DMSO)—(Freeman et al, Antimicrob. Agents Chemother., Vol. 29, p. 730 (1986);

Phosphine oxides—(Bodor and Loftsson, unpublished results);

Dimethylacetamide, dimethyl formamide, pyrrolidones and surfactants—(Barry, Dermatological Formulations—Percutaneous Absorption, Chapter 4, Marcel Dekker, New York (1983)).

Some of the penetration enhancers are too toxic to be used in humans (e.g., dimethyl sulfoxide) or have irritating effects on the skin (e.g., oleic acid and phosphine oxides). In addition, most are not very effective as enhancers or are effective for only a limited number of drugs.

It is an object of the present invention to provide a novel composition and method for enhancing the permeability of topically applied bio-active agents or drugs through skin which are not subject to the above-noted drawbacks.

SUMMARY OF THE INVENTION

These and other objects are realized by the present invention which provides an improved composition adapted for application to the skin of a human or non-human animal and containing a bio-active agent for permeation through the skin, wherein the improvement comprises the presence in the composition of an amount, sufficient to enhance the permeability of the bio-active agent through the skin, of a member selected from the group consisting of (a) a choline ester having the formula:

$$[CH_3(CH_2)_n—COOCH_2CH_2N^+(CH_3)_3]X^{31} \text{ or}$$

$$[CH_3(CH_2)_mCH=CH(CH_2)_n—COOCH_2CH_2N^+(CH_3)_3]X^{31}$$

wherein m and n are integers in the range of from 0 to 30 and $X^-$ is a pharmaceutically acceptable anion and (2) a mixture of the choline ester and an acid having the formula:

$$CH_3(CH_2)_n—COOH \text{ or}$$

$$CH_3(CH_2)_mCH=CH(CH_2)_n—COOH$$

or a pharmaceutically acceptable salt thereof.

An additional embodiment of the invention relates to an improved method for delivering a bio-active agent through the skin of a human or non-human animal comprising applying to the skin a composition adapted for topical application containing the bio-active agent and an amount, sufficient to enhance the permeability of the bio-active agent through the skin, of a member selected from the group consisting of (1) a choline ester having the formula:

$$[CH_3(CH_2)_n—COOCH_2CH_2N^+(CH_3)_3]X^{31} \text{ or}$$

$$[CH_3(CH_2)_mCH=CH(CH_2)_n—COOCH_2CH_2N^+(CH_3)_3]X^{31}$$

wherein m and n are integers in the range of from 0 to 30 and $X-$ is a pharmaceutically acceptable anion and (2) a mixture of the choline ester and an acid having the formula:

$$CH_3(CH_2)_n—COOH \text{ or}$$

$$CH_3(CH_2)_mCH=CH(CH_2)_n—COOH$$

or a pharmaceutically acceptable salt thereof.

A final embodiment of the invention relates to a method of enhancing the permeability of a bio-active agent through the skin of a human or non-human animal from a composition adapted for topical application to the skin comprising incorporating in the composition an amount, sufficient to enhance the permeability of the bio-active agent through the skin, of a member selected from the group consisting of (1) a choline ester having the formula:

$$[CH_3(CH_2)_n—COOCH_2CH_2N^+(CH_3)_3]X- \text{ or}$$

$$[CH_3(CH_2)_mCH=CH(CH_2)_n—COOCH_2CH_2N^+(CH_3)_3]X^{31}$$

wherein m and n are integers in the range of from 0 to 30 and X is a pharmaceutically acceptable anion and (2) a mixture of the choline ester and an acid having the formula:

$$CH_3(CH_2)_n—COOH \text{ or}$$

$$CH_3(CH_2)_mCH=CH(CH_2)_n—COOH$$

or a pharmaceutically acceptable salt thereof.

In the above structural formulas for the choline esters the anion, X, may be any pharmaceutically acceptable anion which is inert with respect to the permeability enhancement characteristics of the ester and with respect to the biological activity of the bio-active agent. Suitable anions include chloride, bromide, iodide, nitrate, phosphate, sulfate, hydrogen sulfate, sulfamates, acetate, propionate, succinate, glycolate, maleate, glutamate, benzoate, sulfanilate, methane sulfonate, etc.

The permeability of any bio-active agent adapted for topical application to the skin of a human or non-human animal will be enhanced by these agents according to the present invention. Suitable such bio-active agents include, e.g., hydrocortisone and its derivatives (and other glucocorticoids); scopolamine, tetracyclines and other antibiotics; nystatin and other antifungal agents; lidocaine and other local anesthetics; propantheline and other anticholinergic agents; salicylic acid and other keratolytic agents; all-trans-retinoic acid (Tretinoin) and other keratoplastic agents; miscellaneous cosmetic agents (e.g., depigmenting agents, depilatories and epilatories); nitroglycerin; antiviral agents (e.g., acyclovir and trifluorothyridine), etc.

There have been no reports in the literature on the direct topical application of choline esters of fatty acids; however, choline laureate has been used in hair conditioners, both in Japan (JP 82109709, 7.8, 1982) and in Germany (G. Lang et al, DE 3440935 Al, 5.15, 1986). It has been used as a bactericide and fungicide (T. Misato et al, JP 7480238, 8.2, 1974) and an an antimicrobial preservative (C. G. Vom Bruck et al., DE 3109188 Al, 9.23, 1982). The compound has also been used in detergents (JP 82143399,A2, 9.4, 1982) and cleaning solutions (JP 8427998 A2, 2.14, 1982). Choline laureate has also been reported to be surface active.

DETAILED DESCRIPTION OF THE INVENTION

In the most preferred embodiment of the invention, the permeability enhancer is choline laureate, oleate, myristate, palmitate or stearate or mixtures of choline laureate and oleic, myristic, lauric, palmitic or stearic acids. Choline laureate and its homologs have been found to be the most effective agents of the choline esters for enhancing the absorption through skin of most bio-active agents. It will be understood, however, that for some topical drugs, other of the herein disclosed choline esters or their mixtures with fatty acids will be more effective.

The proportion of permeability enhancing agent to be included in each composition will depend in each case on the particular bio-active agent present and the concentration and solubility of that agent. It will also depend on the vehicle composition and the nature of the formulation (e.g., liquid, gel, ointment, cream, aerosols and TDDS).

Generally, however, the final composition should contain from about 0.1% to about 15%, by weight, of the permeability enhancing agent to achieve an enhancement of the absorption of the active ingredient. The optimum amount for a particular composition is readily ascertainable by those skilled in the art without the exercise of undue experimentation or inventive faculties having been exposed to the description herein.

Where mixtures of the choline ester and fatty acid are employed, the proportion of ester to acid will again depend upon the particular bio-active agent with which it is admixed and the other parameters described above. Generally, however, a weight ratio of choline ester to oleic acid in the range of from about 3:1 to about 1:3 is suitable.

The compositions, both veterinary and for human use, of the present invention comprise the bioactive agent, the permeability enhancing agent and one or more acceptable carriers therefor and optionally other therapeutic ingredients. The carrier(s) must be "acceptable" in the sense of being compatible with the other ingredients of the formulation and not deleterious to the recipient thereof. The formulations may conveniently be presented in unit dosage form and may be prepared by any of the methods well known in the art of pharmacy. All methods include the step of bringing into association the active agents with the carrier which constitutes one or more accessory ingredients. In general, the formulations are prepared by uniformly and intimately bringing into association the agents with the carrier(s) and then, if necessary, dividing the product into unit dosages thereof.

The dosages of bio-active agent do not form part of the present invention and are well known to those skilled in the art. One of the advantages associated with the present invention, however, is the fact that the amounts of bio-active agent included in the final composition of the invention may be less than in conventional formulations since the permeability enhancing agents ensure a quicker delivery of more active agent across the skin barrier than in conventional systems. Those skilled in the art, having determined the increased rate of permeation resulting from the presence of the permeability enhancing agent will be capable of determining the appropriate dosage of bio-active agent for each composition.

The invention is illustrated by the following non-limiting examples.

EXAMPLE 1

Female hairless mice, strain SKH-1HR-1, were sacrificed by cervical dislocation. The whole dorsal skin was removed, placed carefully over a circular teflon holder, and held in place with an O-ring providing a 7.07 cm$^2$ skin surface. This device was suspended over a 39 ml Plexiglass reservoir (diffusion cells) which was then filled with an isotonic phosphate buffer saline solution containing 0.4% formaldehyde and 0.3% Brij-58. This receptor solution had been sonicated under vacuum to remove dissolved air. The drug to be tested was suspended in the vehicle of choice (see tables) and one or two ml spread over the skin surface. The diffusion cells were placed on magnetic stirrers in a 35° C. incubator containing a pan of water for humidity control and allowed to sit with gentle stirring for 48 hours.

At various time intervals, one ml samples were removed from the cells and replaced with fresh receptor solution. These samples were frozen until analyzed by HPLC. Flux of the drug through the skin was calculated by comparing peak heights of drug to those of standard solutions. The solubilities at 35° C. were determined in the same manner after filtration through 0.45 $\mu$ membrane filter and appropriate dilution. The permeability coefficient was determined by dividing the flux with the solubility or concentration (in the case of nitroglycerin) of the drug in the vehicle. Each experiment was done three times, and the results reported are the mean values ± the standard error.

The samples were analyzed by high performance liquid chromatography (HPLC) methods. For the β-estradiol analysis, the mobile phase consisted of 60% acetonitrile in water and the detector was operated at 280 nm. At flow rate of 1.5 ml/min, the retention time was 3.8 min. For 5604 the mobile phase consisted of 70% acetonitrile in water, and the detector was operated at 243 nm. At flow rate of 2.0 ml/min, the retention time was 3.2 min. For all-trans-retinoic acid, the mobile phase consisted of acetonitrile, tetrahydrofuran, triethanolamine and water (300:20:675), and the detector was operated at 355 nm. At flow rate of 2.0 ml/min, the retention time was 4.0 min. For trifluorothymidine the mobile phase consisted of acetonitrile and 0.05M aqueous potassium phosphate, monobasic (15:85), and the ml/min, the retention time was 3.3 min. For determination of acyclovir an ASI chromosphere 5 m reverse phase column (4.6 mm [i.d.]×25 cm) was used. The mobile phase consisted of 10% acetonitrile in water, and the detector was operated at 254 nm. At flow rate of 1.0 ml/min, the retention time was 4.0 min.

The results are set forth in the following tables.

TABLE 1

The effect of vehicle composition on β-estradiol permeability across hairless mouse skin in vitro. The vehicles were saturated with the drug.

| Vehicle Composition | Cd* (mg/ml) | Flux (mg/cm 2/h) | Permeability Coefficient (cm/n) | P/P$_{PG}$ |
|---|---|---|---|---|
| Propylene glycol (PG) | 100.5 | $4.93 + 0.50 \times 10^{-4}$ | $4.91 + 0.50 \times 10^{-6}$ | 1.0 |
| 2% w/v Choline Laureate (CL) in PG | | $3.23 + 0.82 \times 10^{-3}$ | | |
| 5% w/v Choline Laureate (CL) in PG | 97.8 | $1.18 + 1.53 \times 10^{-2}$ | $1.20 + 0.06 \times 10^{-4}$ | 24.4 |
| 10% w/v Choline Laureate (CL) in PG | 147.5 | $8.13 + 1.53 \times 10^{-3}$ | $5.51 + 1.03 \times 10^{-5}$ | 11.2 |
| 2% v/v Oleic Acid (OA) in PG | 122.6 | $7.61 + 0.52 \times 10^{-4}$ | $6.21 + 0.42 \times 10^{-6}$ | 1.3 |
| 5% v/v Oleic Acid (OA) in PG | 87 | $1.47 + 0.04 \times 10^{-3}$ | $1.69 + 0.01 \times 10^{-5}$ | 3.4 |
| 10% v/v Oleic Acid (OA) in PG | 122.8 | $3.46 + 0.34 \times 10^{-3}$ | $2.82 + 0.28 \times 10^{-5}$ | 5.7 |
| 2% w/v CL and 2% v/v (OA) in PG | 128.2 | $8.76 + 0.07 \times 10^{-4}$ | $6.83 + 0.06 \times 10^{-6}$ | 1.4 |

*Solubility in donor phase (vehicle).
**Permeability coefficient from the vehicle/permeability coefficient from propylene glycol.

TABLE 2

The effect of vehicle composition SAIA* permeability across hairless mouse skin in vitro. The vehicles were saturated with the drug.

| Vehicle Composition | Cd* (mg/ml) | Flux (mg/cm$^1$/h) | Permeability Coefficient (cm/h) | P/P$_{PG}$ |
|---|---|---|---|---|
| Propylene glycol (PG) | 3.31 | $2.01 + 0.36 \times 10^{-5}$ | $6.08 + 1.08 \times 10^{-6}$ | 1.0 |
| 2% w/v Choline Laureate (CL) in PG | 3.31 | $1.90 + 0.38 \times 10^{-4}$ | $5.74 + 1/13 \times 10^{-5}$ | 9.4 |
| 2% v/w Oleic acid (OA) in PG | 3.84 | $2.24 + 0.47 \times 10^{-4}$ | $5.82 + 1.21 \times 10^{-5}$ | 9.6 |
| 2% w/v CL and 2% v/v OA in PG | 4.34 | $3.28 + 0.70 \times 10^{-4}$ | $7.57 + 1.60 \times 10^{-5}$ | 12.5 |

**SAIA is

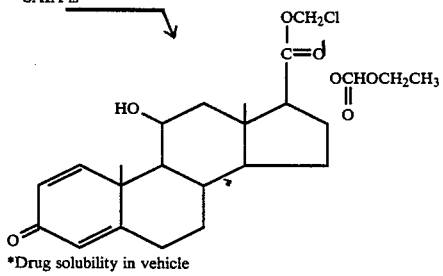

*Drug solubility in vehicle

TABLE 3

The effect of vehicle composition on all-trans-retinoic acid permeability across hairless mouse skin in vitro. The vehicles were saturated with the drug.

| Vehicle Composition | Cd* (mg/ml) | Flux (mg/cm$^2$/h) | Permeability Coefficient (cm/h) | P/P$_{PG}$ |
|---|---|---|---|---|
| Propylene glycol (PG) | 2.08 | $1.55 \pm 0.68 \times 10^{-4}$ | $7.45 \pm 3.27 \times 10^{-5}$ | 1.0 |
| 5% w/v Choline Laureate (CL) in PG | 3.34 | $9.20 \pm 2.76 \times 10^{-4}$ | $2.75 \pm 0.83 \times 10^{-4}$ | 3.6 |
| 2% w/v Choline Laureate (CL) in PG | 3.78 | $1.01 \pm 0.37 \times 10^{-3}$ | $2.66 \pm 0.52 \times 10^{-4}$ | 3.7 |
| 2% w/v CL and 2% v/v Oleic Acid in PG | 3.78 | $5.90 \pm 2.42 \times 10^{-4}$ | $1.56 \pm 0.64 \times 10^{-4}$ | 2.1 |

*Drug concentration in vehicle.

detector was operated at 260 nm. At flow rate of 1.0

TABLE 4

The effect of vehicle composition on nitroglycerin permeability across hairless mouse skin in vitro. The vehicle contained 50 mg nitroglycerin/ml.

| Vehicle Composition | Flux (mg/cm$^2$/h) | Permeability coefficient (cm/h) | P/P$_{PG}$ |
|---|---|---|---|
| Propylene glycol (PG) | $1.10 \pm 0.15 \times 10^{-2}$ | $2.20 + 0.30 \times 10^{-4}$ | 1.0 |
| 5% w/v Choline Laureate (CL) in PG | $0.269 + 0.030$ | $5.39 + 0.61 \times 10^{-3}$ | 24.5 |
| 2% w/v Choline Laureate (CL) in PG | $0.360 + 0.089$ | $7.20 + 1.78 \times 10^{-3}$ | 32.7 |

TABLE 4-continued

The effect of vehicle composition on nitroglycerin permeability across hairless mouse skin in vitro. The vehicle contained 50 mg nitroglycerin/ml.

| Vehicle Composition | Flux (mg/cm$^2$/h) | Permeability coefficient (cm/h) | P/P$_{PG}$ |
|---|---|---|---|
| 5% w/v CL and 5% v/v OA in PG | 0.593 ± 0.050 | 1.19 ± 0.10 × 10$^{-2}$ | 54.1 |

*Drug concentration in vehicle.

TABLE 5

The effect of vehicle composition on trifluorothymidine permeability across hairless mouse skin in vitro. The vehicle was saturated with trifluorothymidine.

| Vehicle Composition | Cd* (mg/ml) | Flux (mg/cm$^2$/h) | Permeability coefficient (cm/h) | P/P$_{PG}$ |
|---|---|---|---|---|
| Propylene glycol (PG) | 146.4 | 2.08 ± 1.92 × 10$^{-3}$ | 1.91 ± 1.31 × 10$^{-5}$ | 1.0 |
| 5% w/v Choline Laureate (CL) in PG | 146.3 | 1.77 ± 1.01 × 10$^{-2}$ | 1.21 ± 0.69 × 10$^{-4}$ | 6.3 |
| 4% Oleic Acid (OA) in PG | 112.2 | 0.461 ± 0.102 | 4.11 ± 0.91 × 10$^{-3}$ | 215.2 |
| 2% w/v Choline Laureate (CL) in PG | 137.4 | 2.47 ± 0.61 × 10$^{-3}$ | 1.80 ± 0.45 × 10$^{-5}$ | 0.9 |
| 2% w/v CL and 2% OA in PG | 136.6 | 0.505 ± 0.005 | 4.02 ± 0.04 × 10$^{-3}$ | 210.5 |

*Drug concentrations in vehicle.

TABLE 6

The effect of vehicle composition on acyclovir permeability across hairless mouse skin in vitro. The vehicles were saturated with acylovir.

| Vehicle Composition | Cd* (mg/ml) | Flux (mg/cm$^2$/h) | Permeability Coefficient (cm/h) | P/P$_{PG}$ |
|---|---|---|---|---|
| Propylene glycol (PG) | 8.13 | | 2.02 ± 0.71 × 10$^{-5}$ | 1.0 |
| 2% w/v Choline Laureate (CL) in PG | 5.29 | —** | —** | |
| 2% v/w Oleic acid (OA) in PG | 4.93 | 1.38 ± 0.17 × 10$^{-2}$ | 2.80 ± 0.34 × 10$^{-3}$ | 138.6 |
| 2% w/v CL and 2% v/v OA in PG | 5.08 | 4.15 ± 0.37 × 10$^{-2}$ | 8.17 + 0.72 × 10$^{-3}$ | 404.5 |

*Drug concentration in the vehicle.
**Very little acyclovir could be detected in the receptor phase and the permeability coefficient could not be detected.

TABLE 7

The effect of vehicle composition on β-estradiol permeability across hairless mouse skin in vitro. The vehicles were saturated with the drug.

| Vehicle Composition | Cd (mg/ml) | Permeability Coefficient (cm/h) ± SD |
|---|---|---|
| Propylene glycol (PG) | 100 | 4.91 ± 0.50 × 10$^{-6}$ |
| 2% v/v oliec acid in PG | 123 | 6.21 ± 0.42 × 10$^{-6}$ |
| 2% w/v choline laureate in PG | 95 | 3.40 ± 0.86 × 10$^{-5}$ |
| 2% w/v choline myristate* in PG | 86 | 1.41 ± 0.21 × 10$^{-5}$ |
| 2% w/v choline palmitate* in PG | 89 | 1.34 ± 0.08 × 10$^{-5}$ |
| 2% w/v choline stearate* in PG | 79 | 3.45 ± 0.90 × 10$^{-5}$ |

*Obtained from Sigma Chemical Company as the iodide salt.

Choline laureate (CL) was much more effective as penetration enhancer for β-estradiol than oleic acid (Table 1). A 5% solution of CL in propylene glycol resulted in about 24-fold increase in flux while 10% oleic acid solution resulted only about 7-fold increase. A 2% CL solution was about as effective as 10% oleic acid solution.

The permeability of a sterodial anti-inflammatory agent (SAIA) through hairless mouse skin is about 25 times lower than β-estradiol. For this compound choline laureate and oleic acid had about the same effect; 2% solutions resulted in roughly 10-fold increase (Table 2). A mixture of 2% choline laureate and 2% oleic acid in propylene glycol gave about a 16-fold increase.

Oleic acid was more effective for nitroglycerin than choline laureate when used alone, 33- and 24-fold increase, respectively, but when a mixture of choline laureate and oleic acid was used, a 54-fold increase was observed.

Oleic acid was also a more effective penetration enhancer for trifluorothymidine permeability across hairless mouse skin. Addition of 4% oleic acid to the propylene glycol vehicle resulted in over 215-fold increase in the flux, and mixtures of 2% choline laureate and 2% oleic acid showed about 210-fold increase (Table 5). The results obtained for acyclovir are displayed in Table 6. Also, here oleic acid was more effective than choline laureate, and combinations of the two penetration enhancers were better than either one of them. After application of saturated solutions (suspensions) of methotrexate in 2% w/v choline laureate and 2% v/v oleic acid or 2% choline laureate or pure propylene glycol, very low levels of methotrexate (less than 0.20-1 μg/40 ml) could be detected after 48 hrs.

EXAMPLE 2

A 15% solution of choline laureate in propylene glycol (almost a suspension) was applied on the lower back of three hairless mice, once every hour for 6 hours, and then once every 24 hours for up to 72 hours. No irritation could be observed; no reddening, no itching, no change in appearance of the skin. The mice continued their normal activity.

A mixture containing 7% w/v choline laureate and 7% v/v oleic acid in propylene glycol was applied on the lower back of three hairless mice every hour as before. Some irritations could be observed after 4 to 5 hours, mainly around rectum and urethra. Some peeling of the skin could be detected the next day.

For comparison, pure propylene glycol was applied on the lower back of three hairless mice as described above.

We claim:

1. In a composition adapted for application to the skin of a human or non-human animal and containing a bio-active agent for permeation through said skin, the improvement wherein said composition contains an amount, sufficient to enhance the permeability of said bio-active agent through said skin, of a member selected from the group consisting of (1) a choline ester having the formula:

$$[CH_3(CH_2)_n-COOCH_2CH_2N^+(CH_3)_3]X^- \text{ or}$$

$$[CH_3(CH_2)_mCH=CH(CH_2)_n-COOCH_2CH_2N^+(CH_3)_3]X^-$$

wherein m and n are integers in the range of from 0 to 30 and X— is a pharmaceutically acceptable anion and (2) a mixture of the choline ester and acid having the formula:

$$CH_3(CH_2)_n\text{-COOH or}$$
$$CH_3(CH_2)_mCH=CH(CH_2)_n\text{-COOH}$$

or a pharmaceutically acceptable salt thereof.

2. The composition of claim 1 wherein said member is said choline ester.

3. The composition of claim 1 wherein said member is a mixture of said choline ester and said acid.

4. The composition of claim 1 wherein said choline ester is choline laureate.

5. The composition of claim 1 wherein said choline ester is choline oleate.

6. The composition of claim 1 wherein said acid is oleic acid.

7. The composition of claim 1 containing from about 0.1 to about 15%, by weight, of said member.

8. The composition of claim 1 wherein the weight ratio of said choline ester to said oleic acid is in the range of from about 3:1 to about 1:3.

9. In a method for delivering a bio-active agent through the skin of a human or non-human animal comprising applying to said skin a composition adapted for topical application and containing said bio-active agent, the improvement wherein said composition contains an amount, sufficient to enhance the permeability of said bio-active agent through said skin, of a member selected from the group consisting of (1) a choline ester having the formula:

$$[CH_3(CH_2)_n-COOCH_2CH_2CH_2N^+(CH_3)_3]X^{31}$$

$$]CH_3(CH_2)_mCH=CH(CH_2)_n-COOCH_2CH_2N^+(CH_3)_3]X^-$$

wherein m and n are integers in the range of from 0 to 30 and X— is a pharmaceutically acceptable anion and (2) a mixture of the choline ester and an acid having the formula:

$$CH_3(CH_2)_n-COOH \text{ or}$$

$$CH_3(CH_2)_mCH=CH(CH_2)_n-COOH$$

or a pharmaceutically acceptable salt thereof.

10. The method of claim 9 wherein said member is said choline ester.

11. The method of claim 9 wherein said member is a mixture of said choline ester and said acid.

12. The method of claim 9 wherein said member choline is choline laureate.

13. The method of claim 9 wherein said ester is choline oleate.

14. The method of claim 9 wherein said acid is oleic acid.

15. The method of claim 9 wherein said composition contains from about 1 to about 15%, by weight, of said member.

16. The method of claim 9 wherein the weight ratio of said ester to oleic acid is in the range of from about 3:1 to about 1:3.

17. A method of enhancing the permeability of a bio-active agent through the skin of a human or non-human animal from a composition adapted for topical application to said skin comprising incorporating in said composition an amount, sufficient to enhance the permeability of said bio-active agent through said skin, of a member selected from the group consisting of (1) a choline ester having the formula:

$$[CH_3(CH_2)_n-COOCH_2CH_2N^+(CH_3)_3]X^- \text{ or}$$

$$[CH_3)CH_2)_mCH=CH(CH_2)_n-COOCH_2CH_2N^+(CH_3)_3]X^-$$

wherein m and n are integers in the range of from 0 to 30 and X— is a pharmaceutically acceptable anion and (2) a mixture of the choline ester and an acid having the formula:

$$CH_3(CH_2)_n-COOH \text{ or}$$

$$CH_3(CH_2)_mCH=CH(CH_2)_n-COOH$$

or a pharmaceutically acceptable salt thereof.

18. The method of claim 17 wherein said member is said choline ester.

19. The method of claim 17 wherein said member is a mixture of said choline ester and oleic acid.

20. The method of claim 17 wherein said choline ester is choline laureate.

21. The method of claim 17 wherein said choline ester is choline oleate.

22. The method of claim 17 wherein said acid is oleic acid.

23. The method of claim 17 wherein from about 1 to about 15%, by weight, of said member is incorporated in said composition.

24. The method of claim 17 wherein the weight ratio of said choline ester to said oleic acid is in the range of from about 3:1 to about 1:3.

* * * * *

UNITED STATES PATENT AND TRADEMARK OFFICE
CERTIFICATE OF CORRECTION

PATENT NO. :     4,892,737
DATED      :     January 9, 1990
INVENTOR(S) :    Nicholas S. BODOR, ET AL It is certified that error appears in the above-identified patent and that said Letters Patent is hereby corrected as shown below:

In claim 1, please substitute the following for the second formula appearing therein:

$$[CH_3(CH_2)_m CH=CH(CH_2)_n\text{-}COOCH_2CH_2N^+(CH_3)_3]X^-$$

In claim 9, please substitute the following for the formulae appearing therein:

$$[CH_3(CH_2)_n\text{-}COOCH_2CH_2N^+(CH_3)_3]X^-$$

$$[CH_3(CH_2)_m CH=CH(CH_2)_n\text{-}COOCH_2CH_2N^+(CH_3)_3]X^-$$

Signed and Sealed this

Fourteenth Day of May, 1991

*Attest:*

HARRY F. MANBECK, JR.

*Attesting Officer*   *Commissioner of Patents and Trademarks*